United States Patent [19]

Borgersen et al.

[11] 4,312,220
[45] Jan. 26, 1982

[54] PORTABLE HARDNESS TESTER

[75] Inventors: Roland Borgersen, Bryn Mawr; James G. Mullen, Bala Cynwyd, both of Pa.

[73] Assignee: King Tester Corporation, King of Prussia, Pa.

[21] Appl. No.: 85,631

[22] Filed: Oct. 17, 1979

[51] Int. Cl.$^3$ .......................... G01D 5/34; G01N 3/42
[52] U.S. Cl. .......................................... 73/81; 73/85; 250/231 SE
[58] Field of Search ............................... 73/81, 85, 83; 250/231 SE

[56] References Cited

U.S. PATENT DOCUMENTS

| | | | |
|---|---|---|---|
| 3,128,621 | 4/1964 | Scott | 73/81 |
| 3,486,373 | 12/1969 | Scott | 73/141 R X |
| 3,728,551 | 4/1973 | Culver et al. | 250/231 SE |
| 3,754,436 | 8/1973 | Saxton | 73/81 |
| 3,815,125 | 6/1974 | May et al. | 250/231 SE X |
| 4,075,478 | 2/1978 | Walker | 250/231 SE |
| 4,147,052 | 4/1979 | Tsujiuchi et al. | 73/81 |
| 4,193,199 | 3/1980 | Whiteley et al. | 250/231 SE X |

Primary Examiner—Daniel M. Yasich

[57] ABSTRACT

A hardness tester includes a frame with a penetrator slidably carried by said frame for movement along a penetration axis, and thereby adapted to form an indentation in a specimen upon application of a load thereto. The resulting depth of the indentation is determinative of the hardness number of the specimen. The means by which a load is applied to the penetrator is rotatably actuated. The rotational displacement of the loading means bears a predetermined relationship to the linear dimension of the indentation depth formed during hardness testing of a specimen. The hardness tester further includes electro-optical mechanical encoding means, and further adapted to emit a coded electrical signal indicative of the sensed angular displacement. Furthermore, an electronic counting circuit decodes the output signals of the encoding means in the form of a count. The count, determinative of the resulting depth of penetration, is indicative of the hardness number of the tested specimen. Optical numerical display means are also provided for visually displaying the specimen hardness number.

16 Claims, 4 Drawing Figures

PORTABLE HARDNESS TESTER

BACKGROUND OF THE INVENTION

The present invention relates to portable hardness testers, and in the particular a hardness tester having electro-optical mechanical encoding means and electronic decoding means responsive to and adapted for determining the hardness of a specimen.

A machine for testing the hardness of a specimen, such as a metal or plastic, is shown and described in U.S. Pat. No. 3,128,621—R. C. Scott, issued Apr. 14, 1964. Such a hardness testing machine utilizes the indentation method for testing the hardness of the specimen, which comprises the forming of an indentation on the specimen by a penetrator of specified shape and material, to which a thrust or a load of predetermined magnitude is applied. The resulting depth of penetration in the specimen is a function of the hardness of the specimen and is measured by means of a hardness number on a particular hardness scale, for example, the normal Rockwell scales being designated B and C. The smaller the depth of penetration the harder the specimen hardness and consequently the larger the numerical value of the hardness number.

In particular, the indentation method requires first the application of a minor load by the penetrator to the specimen, to thereby establish a reference point that minimizes inaccuracies due to surface imperfections in the specimen. Thereafter, a major load is applied to the specimen through the penetrator, thereby enlarging the depth of indentation penetration. The resulting depth of penetration is related to and determinative of the hardness of the specimen. Specifically, the resulting depth of penetration is the linear dimension along the indentation from the point of major loading (the point of maximum penetration) to a point spaced therefrom in the indentation and indicative of the indentation due to the minor load.

The selection of a specific hardness scale depends upon the kind of material to be tested, its previous history with respect to forming, hot and cold working and heat treatment and also its thickness. Each hardness scale requires the use of a specific penetrator and the application of predetermined minor and major loads. The most commonly used normal hardness scales are the Rockwell C and B scales. In particular, the Rockwell C scale is generally used for testing hardened and tempered steels. Its range is from a lower limit of C 20 upwards to about C 70 which is approximately the highest value for hardened steels.

In U.S. Pat. No. 3,486,373, to R. C. Scott, issued Dec. 30, 1969, a variable range load measuring assembly is described for utilization with a hardness tester having a hairpin load spring and of the type described in the aforementioned patent. A load equalizing beam lever is hingedly mounted to the hairpin load spring and by actuation of a hand lever it functions as a load divider thereby extending the number and scope of hardness scales for which the tester may be used. Thus, a hardness tester incorporating this variable range load measuring assembly can test specimens on both the normal and superficial hardness scales without the need of adding, substracting or substituting any part, component or device to the tester either prior to or during the making of the hardness tester.

While the hardness testers described in the heretofore mentioned patents have been used successfully for many years, they nevertheless have some disadvantages. These prior art hardness testers measured or sensed the linear displacement of the penetrator, which is determinative of the hardness number, by means of planetary gears and a rotatable graduated dial system. However, graduated dials and gears can only be made to specific tolerances. In the case of gears, this tolerance deteriorates with the increasing number of gears. Thus, some inaccuracy will result and will be further increased by the wearing down of these elements over years of usage. Also, in reading the hardness scale from the rotatably graduated dial the operator has had to interpret numbers between the graduation points. Thus, the hardness readings from these machines are only accurate to one point.

An object of the present invention is to overcome the inherent disadvantages of the prior hardness testers by incorporating electro-optical mechanical encoding means and electronic decoding means with an optical numerical display in lieu of the gearing and dial system utilized by the prior art. The optical electronic system of the present invention provides a reading more accurate than that which could be provided by the prior art, i.e., a reading accurate to one-half a point on the hardness number scale. Furthermore, the accuracy of the present invention will not deteriorate with usage as do the prior art machines, since it is an electronic means and not a mechanical means which senses the depth of penetration which is determinative of the hardness number. As the electronically determined hardness number is numerically displayed to onehalf a point of the hardness number, the operator need not make a transposition judgment as he did with the prior art devices utilizing a graduated dial.

These and other advantages of the present invention will become more apparent from the subsequent description of the present invention.

BRIEF DESCRIPTION OF THE INVENTION

The hardness tester of the present invention includes a frame having a penetrator slidably mounted on the frame for movement along a penetration axis. The penetrator is movable along the axis for the purpose of indenting a specimen upon the application of a predetermined load thereto. The resulting indentation depth along the penetration axis is determinative of the hardness of the specimen. Loading means are also provided for applying the predetermined load to the penetrator and thereby moving the penetrator along the axis. Rotatable means are utilized for actuating the load means. The rotational displacement of the loading means has a predetermined correlation with the linear dimension of the indentation depth along the penetration axis. Operatively associated with the loading means is an electro-optical mechanical encoding means for sensing the angular displacement of rotation of the loading means. The encoding means includes an emitting means adapted to emit encoded electrical output pulses indicative of the sensed angular displacement. Electronic means receptive to the encoded output signal indicative of the resulting depth of penetration are further provided for decoding the electrical impulses to a relative count or intermediate electrical signal equivalent to the hardness number of the specimen. The decoded signals are electronically connected to an optical numerical display means for driving such means and thereby display the specimen hardness number thereon.

DETAILED DESCRIPTION OF THE INVENTION

Figure 1:
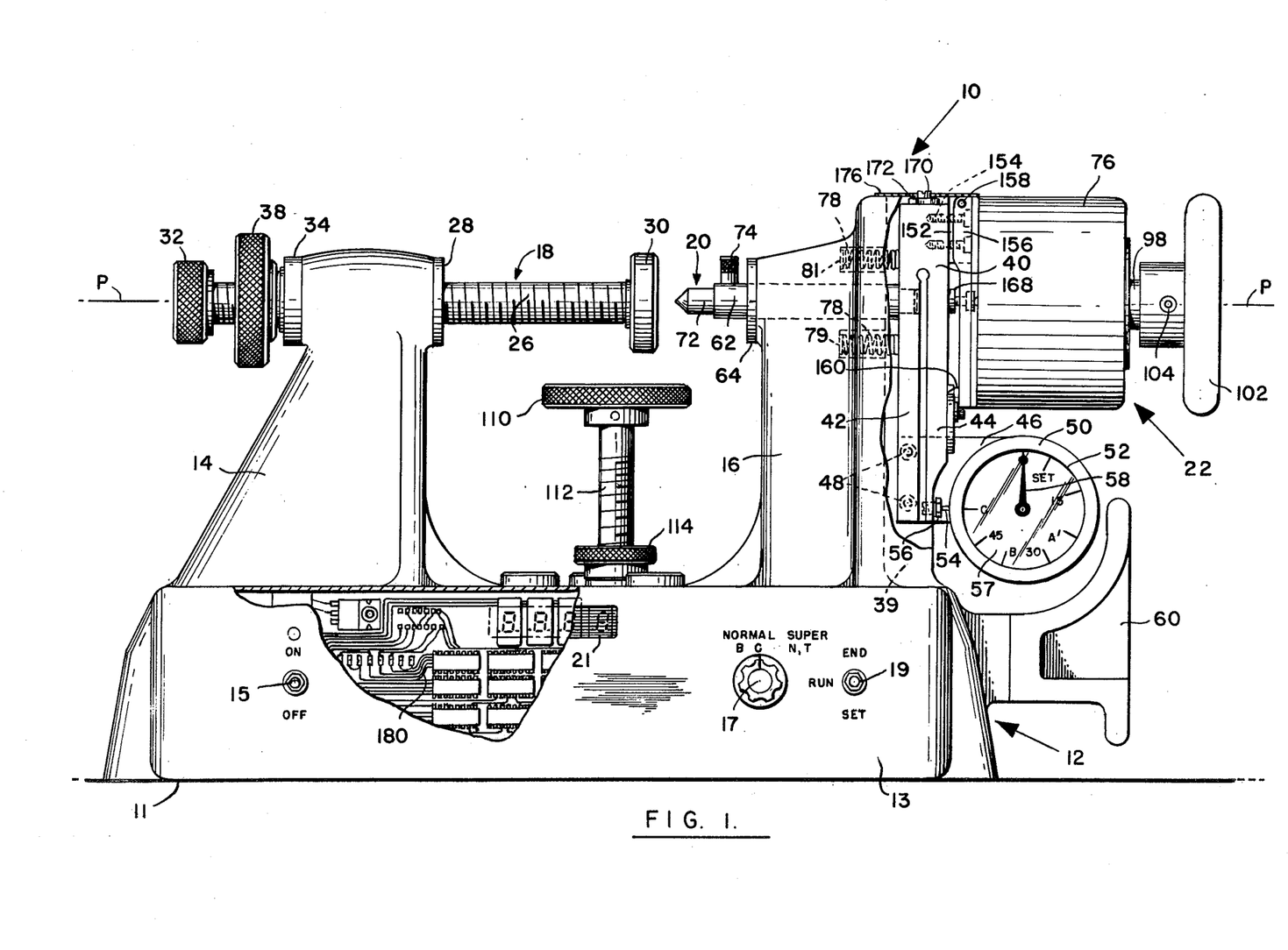
FIG. 1 is a side elevational view of one embodiment of the hardness tester of the present invention.
Figure 2:
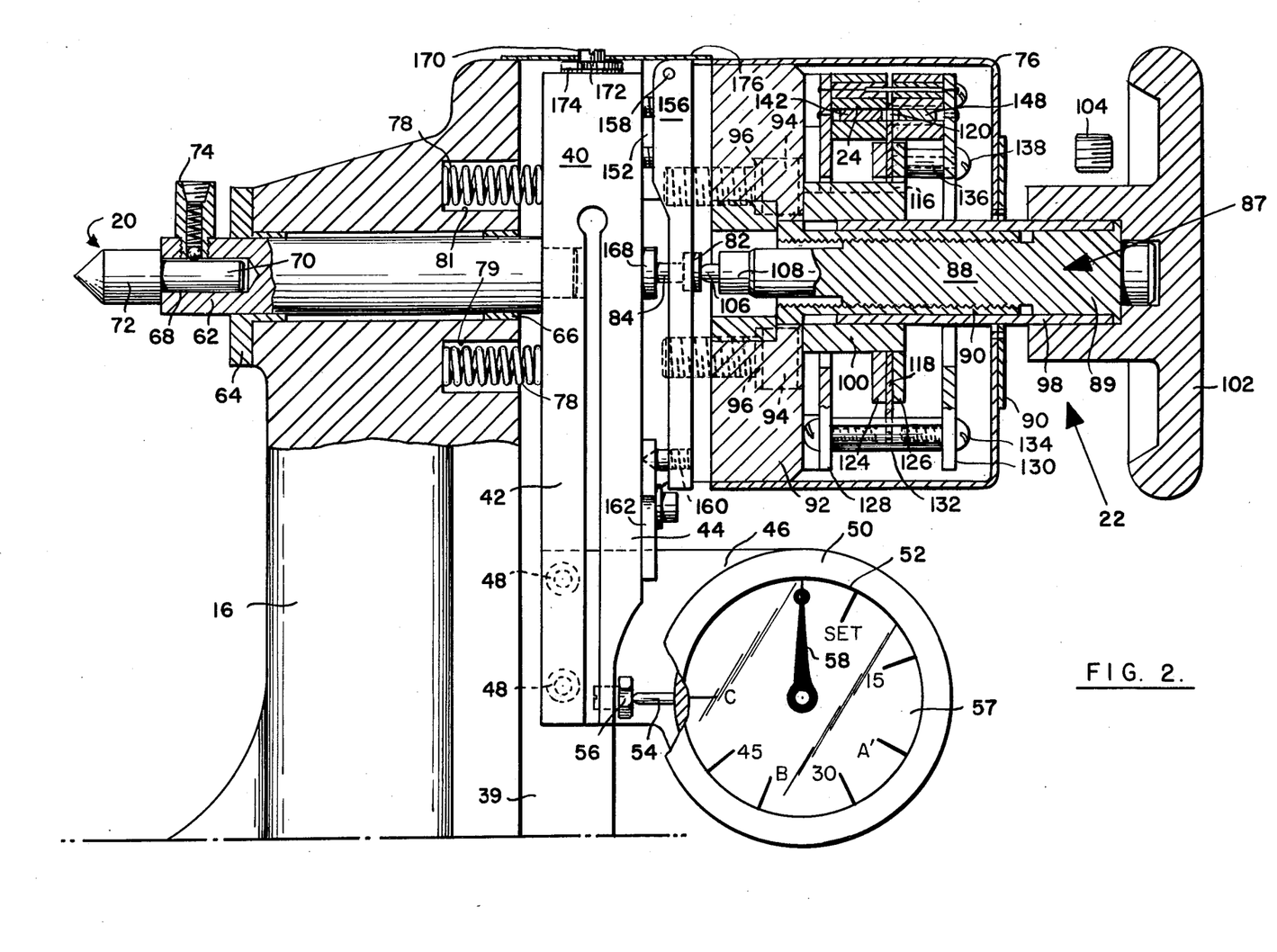
FIG. 2 is an enlarged cross-sectional view of a portion of the hardness tester shown in FIG. 1.
Figure 3:
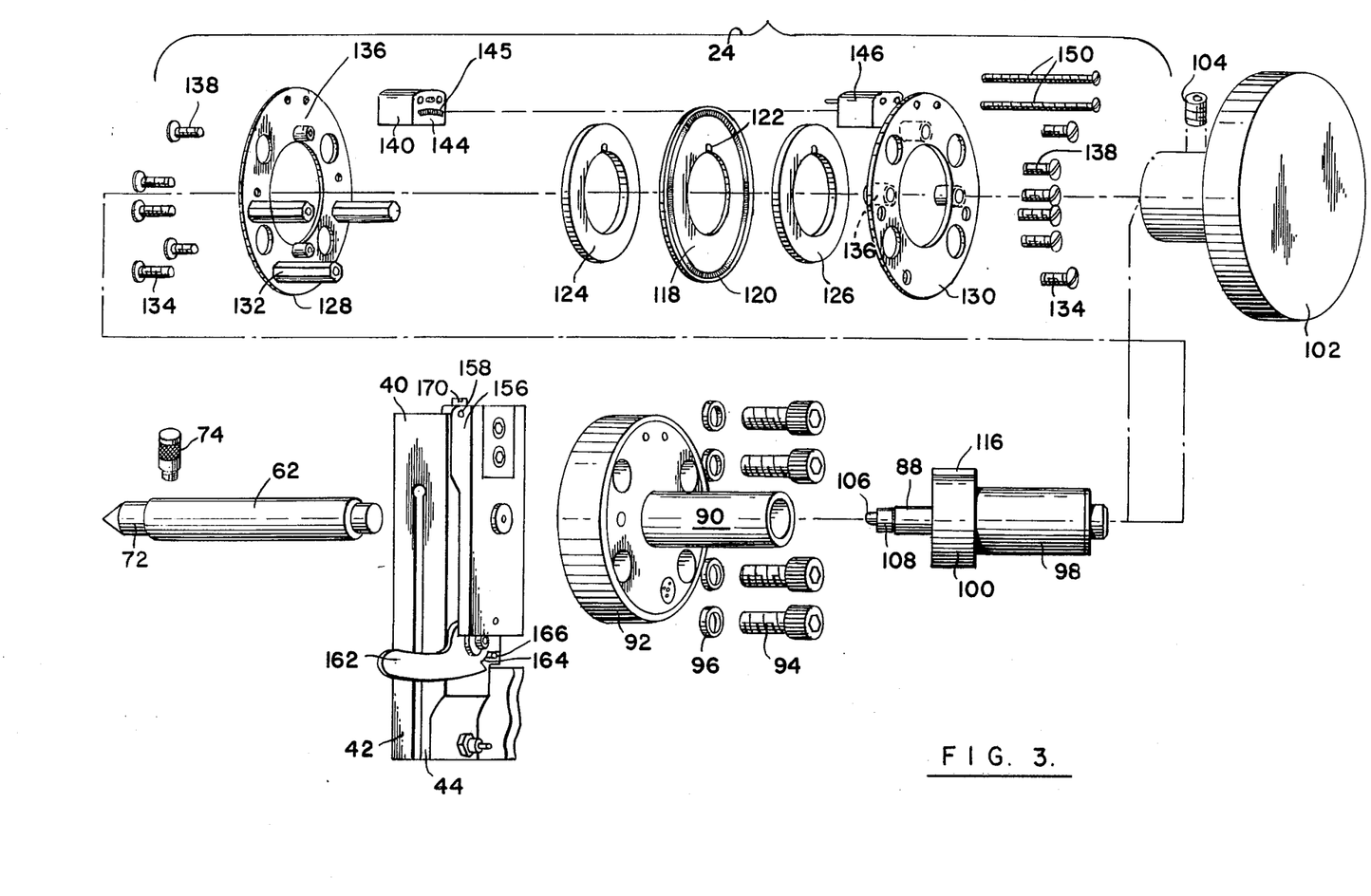
FIG. 3 is an exploded view of portions of the hardness tester shown in FIG. 2.

Referring to FIGS. 1 to 3, the portable hardness tester of the present invention is generally designated 10. Hardness tester 10 includes a frame 12 having a base 11 and first and second vertically extending support members 14 and 16. Typically, the frame 12 is cast of a lightweight high tensile strength material such as aluminum alloy. Mounted on the base 11 of frame 12 is a housing 13 into which is placed a substantial portion of the electronic circuitry of the tester 10. On the housing 13 are an on-off power switch 15, for activation of the electronic circuitry in the present invention, a hardness scale section dial 17, a count set switch 19, and an optical numerical display 21 typically comprising four alpha-numeric LED's. The operation and function of these elements will be apparent from the subsequent description of hardness tester 10.

First and second vertically extending support members 14 and 16 are spaced apart, with the first member 14 supporting a first anvil spindle assembly 18. Second member 16 supports a penetrator assembly 20, a penetrator loading assembly 22 and an electro-optical mechanical encoding assembly 24. These assemblies are aligned on a common penetration axis, designated P.

The first anvil spindle assembly 18 includes an anvil spindle 26, which is precision threaded throughout its length for engagement with a mating thread formed through a spindle bushing 28 fixed into the first vertically extending support member 14. The spindle 26 carries at one end thereof an anvil 30 for supporting a specimen which is to be hardness tested. An actuation knob 32 is press-fitted to the spindle 26 at an end opposite anvil 30 and serves as a gripping means for effecting rotational movement of the spindle 18 along the penetration axis P. The spindle bushing 28 receives a bushing lock nut 34 in threaded engagement thereon. The spindle bushing 28 is press-fitted into the first member 14 and is secured into position by the bushing lock nut 34, and by a drive pin, which is not shown. A spindle lock nut 38 is in threaded engagement with the spindle 26 and positioned between knob 32 and bushing lock nut 34. Once the specimen is positioned with the spindle assembly 18, spindle lock nut 38 is threaded on the spindle 26 against the bushing lock nut 34 in order to lock the spindle 26 in position by forcing the thread faces of spindle 26 and bushing 28 together in a direction and manner that precludes relative movement between the spindle 26 and bushing 28 when a load is applied to the specimen during hardness testing.

As described the specimen which is to be hardness tested is held against the face of anvil 30, but it may also be supported by a second anvil 110, which like the first anvil 30 has a flat smooth surface. A supporting spindle 112 is in threaded engagement with the frame 12 at the base 11 and supports the second anvil 110. A lock nut 114 is in threaded engagement on the supporting spindle 112 in order to secure the second anvil 110 in a vertically adjusted position by the locking engagement of the number 114 with the frame 12.

Positioned into a recess 39 in the second vertically extending support member 16, and floatable therein along the penetration axis P, is a spring member 40. Usually the spring member 40 is constructed of beryllium copper and fabricated to provide elastic deflection with negligible hysteresis error and drift under maximum loading. Spring member 40 is generally of a hairpin configuration having first and second legs 42 and 44. The button 168 is mounted to leg 44 of spring member 40 at its intersection with the penetration axis.

A dial bracket 46 is attached to first leg 42 by means of screws 48 and extends past second leg 44. Secured to dial bracket 46 as it extends past leg 44 is dial compression indicator 50, having a rotatable bezel 52 for adjusting the relative position of the dial pointer 58 to a calibration point on the scale 57. A spring-load indicator shaft 54 extends from the dial compression indicator 50 and rests on the flat surface of a button 56 which is screwed into the bottom end of second leg 44. The indicator shaft 54 and button 56 are in contact with each other and are so arranged that the slightest flexure of the spring member 40 due to compression will cause the dial pointer 58 to turn in a clock-wise direction and thus indicate the compression load on scale 57.

An indicator guard bracket 60 is secured to and extends from frame 12 in order to partially surround the dial indicator 50 and thereby protect this sensitive instrument from inadvertent jarring.

Attached to the upward end of the spring member 40 is a hinge block 152 which is securely fastened to spring member 40 by machine screws 154. A load equalizing beam 156 is hingedly mounted to the hinge block 152 by means of hinge pin 158. The load equalizing beam 156 is typically made of stainless steel and is dimensionally constructed for negligible deflection for the maximum value of load applied.

On the side of the load equalizing beam 156 farthest from spring member 40 and at its point of intersection with the penetration axis, P, a ball seat (FIG. 2) is mounted thereto. A stem 84 extends from ball seat 82 and through the beam 156 to contact button 168 on spring member 40.

At the free end of the equalizing beam 156, a load pin 160 is threaded into a hole located at the longitudinal center and spaced so that its distance from the penetrator axis P is equal to the distance from the hinge pin 158 to the penetrator axis P.

A manual lever 162 having an extending handle is disposed between spring member 40 and load pin 160 and is fastened to the spring member by conventional fastening means. Partial angular displacement of the manual lever 162 is provided by means of a recess 164 (FIG. 3) and a stop pin 166 (FIG. 3) which is press fitted into leg 44 of spring member 40.

Manual lever 162 also includes a second recess (not shown) into which the load pin 160 enters when the manual lever 162 is in its uppermost position; this is the position for determining a hardness number on one of the normal hardness scales. The length of the load pin 160 is adjusted so that while extending into the second recess it does not make contact with spring member 40. However, upon moving the manual lever 162 to its lowest position (this is the position for using the superficial hardness scales) the load pin 160 is moved out of the second recess and makes contact with a surface of manual lever 162 so as to slightly rotate the load equalizing beam 156 about the hinge pin 158. In this slightly rotated position the stem 84 of the ball seat 82 is no longer in contact with the button 168 disposed on leg 44 of the spring means 40 at the penetration axis, P.

As will be more readily apparent from the subsequent discussion, a load is applied by the penetrator loading assembly 22 to the spring member 40 at the button 168 when manual lever 162 is positioned for testing with use of a normal hardness scale. However, when lever 162 is positioned for testing with use of a superficial hardness scale the load is applied to spring member 40 at the end of leg 44 by load pin 160 contacting manual lever 162. Thus, the beam 156 functions as a load divider to extend the number or scope of hardness scales for which the tester 10 may be used, i.e. the tester may be used for testing with either the normal or the superficial hardness scales.

Placed in each of two horizontally disposed and spaced apart recesses 79 and 81 in second support member 16 are return springs 78. Return springs 78 each bear upon second support member 16 and upon the spring member 40, one at leg 42. As will be more readily apparent from the subsequent discussion of the present invention, return springs 78 move the penetrator assembly 20 out of contact with the specimen after completion of the hardness testing procedure.

The penetrator assembly 20 includes a penetrator extension rod 62 which is slidable along bushings 64 and 66, each of which is press-fitted into the second support member 16. One end of the penetrator extension rod 62 is press-fitted into second leg 42 of spring member 40. Thus spring member 40 floats in recess 39, supported by extension rod 62 as the rod 62 moves along bushings 64 and 66. The opposite end of extension rod 62 is provided with a cylindrical hole 68 into which is fitted the stem portion 70 of a conventional penetrator 72. A screwably actuated ball plunger 74 is utilized to secure the penetrator 72 in place by applying a pressure from a steel ball in the plunger 74 onto a flat surface of the stem portion 70 of penetrator 72. Typically, the penetrator will be of a conventional type, such as a hardened steel ball, a sphero-conically shaped diamond, or some other well known type and shape of penetrating tool.

A penetrator travel indicator 170 is fixed to the top surface of spring member 40 and is visible at the top side of the hardness tester 10. Typically, the penetrator travel indicator 170 includes a screw-like member 172 threaded into the top surface of spring member 40 with a washer member 174 interposed therebetween. Screw-like member 172 is slidable in a slot formed on an indicator plate 176 fastened to support member 16 at the top of the recess 39. Two indication marks are etched along the slot in indicator plate 176. The indicator mark most towards the left is identified as the "maximum" mark while the indicator mark most to the right is identified as the "minimum" mark. The purpose of travel indicator 170 is most apparent when an operator is placing a specimen in the tester 10. At such time the operator must view the penetrator travel indicator 170 to make certain that it is positioned somewhere between the two indication marks prior to beginning the hardness testing. If the penetrator travel indicator 170 extends in a leftward direction beyond the "maximum" mark, this is an indication that spring member 40 may be abutting second support member 16, in which case accurate loading of the penetrator 72 is not possible. If the penetrator travel indicator 170 extends in a rightward direction beyond the "minimum" mark, portions of the electro-optical mechanical encoding assembly 24 may be damaged by excessive rightward movement of portions of the penetrator load assembly 22.

A cylindrical hollow cap 76 is firmly and slidably held onto the second vertically extending support member 16. Housed in the cap 76 is the electro-optical mechanical encoding assembly 24 and some elements of the penetrator load assembly 22.

That portion of the penetrator load assembly 22 housed within the cap 76 includes a spindle assembly 87 having a male load spindle 88. The male load spindle 88 is threaded along the central portion of its length; such portion of spindle 88 is typically one-half inch in outer diameter and machined to forty threads per inch. At the end of load spindle 88 which extends beyond cap 76 there is formed an unthreaded section 89 having an enlarged diameter.

Press fitted to shoulder section 89 and spaced from the threaded surface of spindle 88 is outer sleeve member 98. At the left hand end of outer sleeve member 98, there is fixedly mounted an annular member 100 having a longitudinally extending keyway projection 116. Annular member 100 does extend somewhat beyond the left hand end of outer sleeve member 98.

Interposed between male load spindle 88 and sleeve member 98, for threaded engagement with male load spindle 88 and slidable contact with sleeve member 98, is female spindle 90. At one end of female spindle 90 a shoulder of an enlarged diameter is formed and is press-fitted into a disk-like member 92. The disk-like member 92 is attached to a second support member 16 by means of bolts 94 and washers 96. Generally the bolts 94 are of the socket head variety. Accordingly, female spindle 90 is stationary with respect to support member 16 while male load spindle 88 is capable of threaded movement therethrough.

A handwheel 102 is slidably received onto that section of outer sleeve member 98 extending beyond cap 76 and is secured thereto by one or more set screws 104. Thus, rotation of handwheel 102 causes rotational engagement of the threads of male and female spindles 88 and 90, with the consequential linear displacement of male load spindle 88.

The end of male spindle 88 housed within the cap 76, is seated to conform to the contour of a hardened steel ball 106, which is held in position at the end of the spindle 88 by a press-fitted retaining sleeve 108. Male load spindle 88, penetrator 72 and penetrator extension rod 62 are in alignment with each other along the penetration axis, P. Spring member 40 is interposed between male load spindle 88 and the penetrator extension rod 62 so that ball 106 can contact ball seat 82 along the penetration axis, P, upon forward rotational movement of handwheel 102. As is apparent from the heretofore discussion of the present invention, spring member 40 serves both as means to transfer the load applied by the male load spindle 88 to the penetrator 72, as well as a means to measure the applied load.

The electro-optical mechanical encoding assembly housed in cap 76 includes an annular shaped encoding disk 118 having a predetermined plurality of radially extending slots 120 in close proximity to its outer periphery. A keyway 122 is formed in the inner periphery of encoding disk 118. Typically, 640 slots, about 0.060 inch long and 0.006 inch wide are formed in encoding disk 118, however, slots 120 may be of a different predetermined number.

Encoding disk 118 is sandwiched between gasket members 124 and 126. Each gasket is of a soft or rubber like material having an inside diameter and keyway formed therein equivalent in its dimensions to the inside diameter and keyway of encoding disk 118. The outer diameter of gasket members 124 and 126 must be smaller than the outside diameter of the disk 118 so as not to cover slots 120. Encoding disk 118 and the gaskets 124 and 126 are slidably mounted onto annular member 100 such that keyway projection 116 is in alignment and contact with keyway 122 of disk 118 and the keyways of gasket members 124 and 126. Thus, rotational movement of the male spring assembly 87 will further result in the rotational movement of encoding disk 118 and gaskets 124 and 126.

Electro-optical mechanical encoding assembly 24 further includes spaced-apart first and second annular members 128 and 130. Annular members 128 and 130 are retained in their spaced-apart relationship by means of a plurality of horizontally disposed spacers 132 which are mounted to each of the annular members 128 and 130 by means of screws 134. Encoding disk 118 and gaskets 124 and 126 are interposed between first and second annular members 128 and 130 by means of spacers 136. The spacers 136 come in contact with the gaskets 124 and 126, and are attached respectfully to the first and second annular members 128 and 130 by means of screws 138.

Mounted to first annular member 128 is a light emitter housing 140 having two light emitting devices 142 mounted in a recess therein and disposed so as to emit their light outward from the recess. The light emitting devices are, for example, light emitting diodes (LED's) identified as 5082-4658 and manufactured by Hewlett Packard. A mask member 144, having a radial segment of slots 145 formed therein is mounted onto light emitter housing 140 so that slot segment 145 extends across the recess of housing 140 and is in a position opposite slots 120 of encoding disk 118.

Mounted onto the second annular member 130 is a light receiver housing 146 having a recess formed therein to carry two light sensing devices 148 such as Photodarlington transistors identified as 2N5777 and manufactured by Motorola Corporation. Upon receiving and sensing a light signal, the light sensing devices emit an electrical output signal indicative of the sensed light, i.e. a pulse of light sensed by the light sensing devices generates the emission of an electrical pulse.

A pair of relatively long screws 150 pass through openings in first and second annular members 128 and 130, light emitting housing 140 and light receivig housing 146, and are screwed into threaded openings in the disk-like member 92 so as to retain these elements in a fixed and stationary position thereon. While slots 145 are dimensionally equivalent to slots 120, the spacing between slots 145 differs from that of slots 120. Furthermore, slots 145 are stationary with respect to frame 12 while slots 120 are capable of rotational movement.

The light emitting and receiving devices are in optical alignment with each other, however interposed therebetween are the stationary slots 145 and the movable slots 120. Therefore, as light beams are emitted from the two light emitting devices in housing 140 they will become collimated as they pass through the stationary slots 145. Assuming that the slots 120 are in movement across the path of this collimated light a light interference pattern is generated the result of the Moire effect, i.e. the difference in spacing between stationary slots 145 and movable slots 120 results in a 90° phase shift. This effect is more apparent if we examine the interference pattern at a specific instance of time. In particular, assuming that there has been a rotation of the movable slots 120 equal to approximately the width of one of the slots, the resulting interference pattern comprises a light pulse being sent to one of the two light receiving devices while the other device receives no light impulse. Now, assuming a second movement of the movable slots 120 equivalent to approximately that of one slot, the interference pattern is changed such that the light receiving device which had before seen a light pulse now sees no light, whereas the other light receiving device now receives a light pulse. Thus, for every movement of the movable slots 120 equivalent to one slot, an output signal in the form of an electrical pulse will be emitted from one of the light receiving devices while the other receiving device will emit no electrical signal. This signal pattern is reversed upon each movement of the slots a radial distance equivalent to approximately the width of one of the slots. Thus, the two output signals emitted from the light receiving devices are actually digital binary information signals of two bits. These digital signals are thereafter sent to a counting circuit which will subsequently be discussed.

The digital binary information signals emitted from the two light sensing devices are sent by means of a wire bundle (not shown) to a conventional electronic counting circuit 180. Counting circuit 180, disposed in housing 13, counts the number of segments through which the disk 120 has been rotated by counting the changes in the digital binary information signals received. That is to say, the first binary signal which it receives could be in a form equivalent to 0-1. However, upon rotating the disk a distance equal to approximately one slot, the interference pattern causes a reversal in the binary signal so that the counting circuit now reads a signal such as 1-0. Each change in signal is counted by the counting circuit 180 and the total count is thus indicative of the number of slots through which the encoding disk 120 has been rotated.

If one reversed the direction of disk 118 rotation, i.e. by changing the rotation of the handwheel 102, conventional logic gating circuitry which comprises a portion of the counting circuit 180, senses this change in direction. The logic circuitry is constantly testing the binary information signal pattern and any change in this pattern is sensed as a change in direction of rotation. Thus, the counting circuit 180 counts the number of slots 120 through which the disk 118 is rotated and further resolves the direction of rotation.

It is the electro-optical mechanical encoding assembly which encodes the angular movement of the handwheel 102, male spindle 88, and disk 118 into a number of electrical impulses or signals, while the counting circuit 180 decodes these signals into a count. Since there is a fixed relationship between the linear resulting depth of penetration of penetrator 72 into a specimen and the angular rotation of handwheel 102 and disk 118, a predetermined numerical relationship will exist between the resulting count of counting circuit 180 and a specific hardness number on a specific hardness scale. More particularly, since we know the threads per inch on male spindle 88, and the number of slots through which disk 118 must be rotated to complete one full rotation, and since the linear displacement of the spindle 88 has a fixed relationship to the linear displacement of penetrator 72, it is apparent that a specific count of the number of slots through which disk 118 has been rotated bears a predetermined relationship to the resulting depth of penetration and consequently the hardness number of the tested specimen.

One factor in determining the number of slots formed in the encoding disk 118 relates to the accuracy and precision of tester 10. It is most convenient if the resulting depth of penetration in a specimen can be accomplished by rotation of the handwheel 102 less than one full revolution. Thus, only a portion of the slots 120 will be counted by counting circuit 180, therefore the more slots present, the more accurate the count which is representative of the rotational displacement of the handwheel 102.

Counting circuit 180 further includes or is powered by a conventional power source which is activated by the on-off power switch 15.

Counting circuit 180 also includes conventional circuitry for driving a plurality of optical numerical display devices 21 such as LED's. This conventional circuitry converts the binary information signals or count into an arithmetic number displayed by the optical numerical display devices. This displayed number is the hardness number of tested specimen.

In operating the present invention, rotation of the handwheel 102 in the clockwise direction causes the male load spindle 88 to move towards the left and thereupon contact the spring member 40, whereupon the applied load is transferred to the penetrator assembly 20 which is moved to the left along the penetration axis P, and into indenting contact with the specimen. This movement is initially resisted by the pair of return springs 78.

Therefore, upon disposing a specimen, such as a knife blade, onto the first and second anvils 30 and 110, the penetrator assembly 20 and specifically the penetrator 72, is moved along the penetration axis P by actuation of handwheel 102 until it makes initial contact with the specimen. This point of first contact is known to those skilled in the art as the "dead zero load"; at this instance there is no deflection of spring member 40. At "dead zero load" the rotatable bezel 52 on the indicator 50 is adjusted so that the dial pointer 58 indicates a zero load point on scale 57. For the purpose of describing the present invention, it is assumed that the specimen calls for a hardness reading on the Rockwell C scale; thus, the hardness scale dial 17 is set to the "Normal C" reading.

Further rotation of handwheel 102 in the clockwise direction causes further movement of the penetrator 72 along the penetrator axis and resistance to its movement by the specimen. The resulting resistance causes spring member 40 to compress, and this compression is indicated by movement of pointer 58 on dial indicator 50. The operator continues the motion of penetrator 72 along the penetration axis and into the specimen until pointer 58 indicates the "Set" load calibration point on scale 57, whereupon he actuates the count momentary switch 19 to its "Set" position. A "Set" reading on scale 57 is indicative of the application of a minor load to the specimen. Assuming that the specimen calls for a reading on the Rockwell C scale, the minor load is equivalent to 10 kilograms. Actuating count momentary switch 19 to the "Set" position activates conventional circuitry in count circuit 180 to cause a predetermined count to be read by the count circuit 180 and displayed by the LED's 21. This predetermined count is a function of the hardness scale used and is the starting or reference point for commencement of the hardness test. More specifically, this predetermined count adjusts the count of counting circuit 180 so that the hardness number of the specimen as determined by the count of count circuit 180 is in accordance with the selected hardness scale. The predetermined count will be different for each of the various hardness scales.

Thereafter, the load on the penetrator 72 is increased by the continued clockwise rotation of handwheel 102, resulting in increasing depth of penetration of penetrator 72. As heretofore discussed, the count circuit 180 will continue to count to a number indicative of the angular displacement of handwheel 102, and such count is displayed by an arithmetic reading on LED's 21.

The load applied by penetrator 72 is continued until a major load is applied to the specimen. Since hardness is to be measured on the Rockwell C scale the load is increased until the pointer 58 indicates "C" on scale 57; this is indicative of a major load of 150 kilograms. The count of count circuit 180 has, of course, continued as the penetrator 72 has been displaced from its minor load or starting position to its major load position.

Penetrator 72 is now withdrawn from its major load position in the specimen, by reversing the direction of handwheel 102 rotation, i.e. counter-clockwise. The counting circuit 180 senses this change in direction and the direction of the count is accordingly changed. That is to say, if the count was in an upward direction, reversing the direction of rotation of handwheel 102 causes the count to decrease in number. The operator continues to withdraw penetrator 72 from the indentation in the specimen until the pointer 58 of dial 50 returns to its "Set" position. At this position the count of the count circuit 180, as displayed on the LED's 121, is the actual hardness number of the specimen. Thus, it is apparent that the resulting depth of penetration, determinative of the hardness number, is that linear distance travelled by the penetrator, from the point at which a major load was applied to the specimen back to a point (spaced somewhere in the identation) at which the indicator dial 50 exhibits the application of a minor load on the penetrator 72.

Once the display devices 21 display the actual hardness number, the operator will actuate count switch 19 to its "End" position. Such actuation disconnects the display devices 21 from the actual counting of the count circuit, so that the inadvertent movement of handwheel 102 will not change the now determined hardness number of the specimen.

Figure 4:
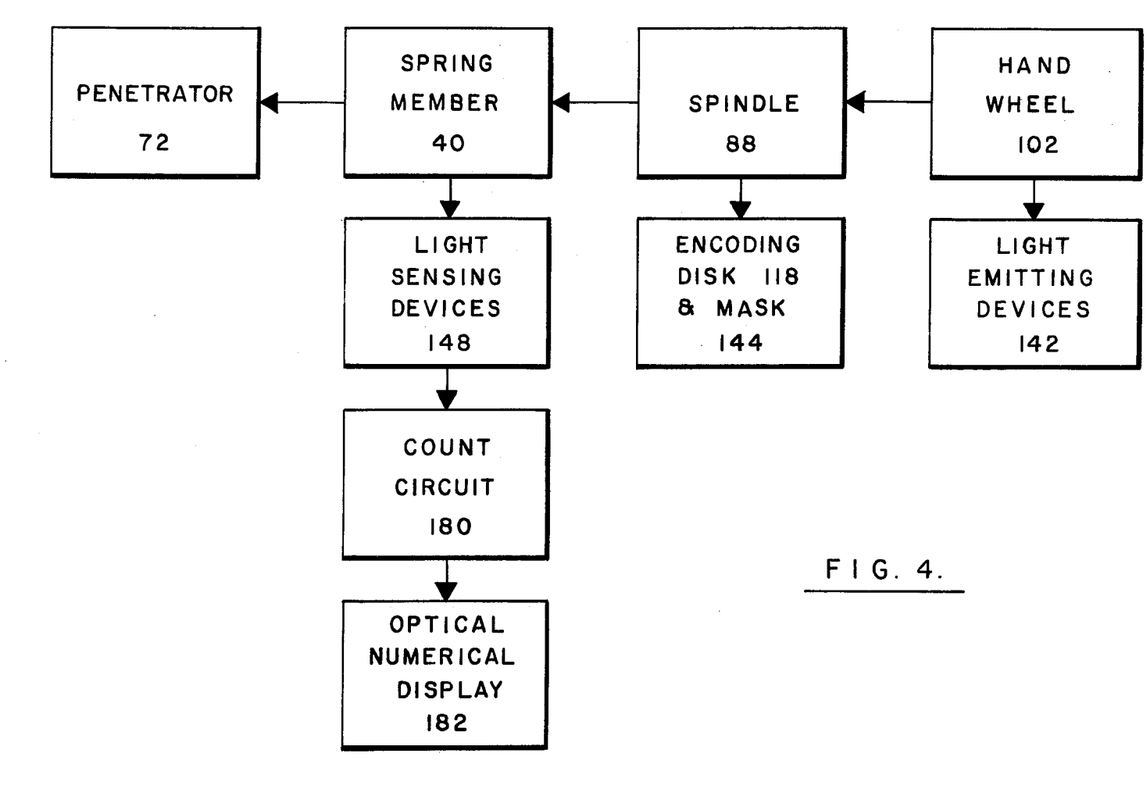
FIG. 4 is a block diagram showing the interrelationship and cooperation between numerous elements of the hardness tester of the present invention.

FIG. 4 is a block diagram of the major elements of the present invention, and therein shows their interrelationship and interaction with each other.

While this invention has been described with respect to a specific embodiment, it is not limited thereto. The appended claims therefore are intended to be construed to encompass all forms and embodiments of the invention, within its true spirit and scope, whether or not such forms and embodiments are suggested herein.

I claim:
1. A hardness tester comprising:
   a. a frame, including means for holding a hardness test specimen;
   b. a penetrator slidably mounted in an assembly on said frame for linear movement along an axis, for indenting said specimen;

c. loading means for applying a predetermined load to said penetrator in a direction parallel said axis, when said penetrator has contacted said specimen;

d. rotatable means for actuating said loading means, angular displacement of a rotatable portion of said actuating means from a reference position defined by said penetrator contacting said specimen before said predetermined load is applied to said penetrator having a predetermined correlation with linear penetration of said specimen by said penetrator moving along the penetration axis when said predetermined load is applied to said penetrator;

e. electro-optical mechanical encoding means connected to said actuating means for producing electrical coded signals proportional to angular displacement of said rotatable portion of said actuating means;

f. receiving means for converting said output electrical signal to an intermediate electrical signal corresponding to the hardness number of the specimen; and g. optical display means for receiving said intermediate signal and for visually displaying the specimen hardness number.

2. A hardness tester comprising:

a. a frame including means for holding a hardness test specimen;

b. a penetrator slidably mounted in an assembly on said frame for linear movement along an axis, for indenting said specimen;

c. loading means for applying a predetermined load to said penetrator in a direction parallel said axis, when said penetrator has contacted said specimen;

d. rotatable means for actuating said loading means, angular displacement of a rotatable portion of said actuating means from a reference position defined by said penetrator contacting said specimen before said predetermined load is applied to said penetrator having a predetermined correlation with linear penetration of said specimen by said penetrator moving along the penetration axis when said predetermined load is applied to said penetrator;

e. electro-optical encoding means for sensing any rotation of said actuation means, including:
  i. a pair of light radiation emitting devices;
  ii. a pair of light radiation sensing devices in optical alignment with said light emitting devices, said sensing devices adapted for emitting an output electrical signal indicative of the light sensed;
  iii. a mask member, fixedly disposed between said light emitting and said sensing devices, said mask member having formed therein a plurality of radially extending slots optically aligned with said light radiation emitting and sensing devices;
  iv. an annularly shaped encoding disk having a plurality of slots formed along its periphery, said encoding disk mounted on said loading means and rotatable therewith, said encoding disk slots disposed between and in optical alignment with said mask member slots and said light radiation sensing means, spacing between said mask member slots differing from the spacing between said disk slots such that upon emission of light from said emitting device through said mask and disk slots a light interference pattern falls on said light radiation sensing devices, said interference pattern changeable with each rotation of said disk through an angular distance substantially equal to one disk slot, said changeable light radiation interference pattern adapted to cause said light radiation sensing means to emit electrical signals in the form of digital binary information signals upon rotation of said disk an angular displacement substantially equal to one disk slot;

f. receiving means for converting said output electrical signal to an intermediate electrical signal corresponding to the hardness number of the specimen; and g. optical display means for receiving said intermediate signal and for visually displaying the specimen hardness number.

3. The hardness tester in accordance with claim 2, wherein said light radiation emitting devices are light emitting diodes.

4. The hardness tester in accordance with claim 2, wherein said light radiation sensing devices are photodiodes.

5. The hardness tester in accordance with claim 2, wherein the spacing between said mask member slots is greater than the spacing between said disk slots.

6. The hardness tester in accordance with claim 2, wherein said electronic means comprises an electronic circuit adapted for counting said binary signals, each count being representative of the angular displacement of said encoding disk of approximately one disk slot, and the count indicative of the resulting depth of penetrator penetration being representative of the hardness number of the specimen.

7. The hardness tester in accordance with claim 6, wherein said counting circuit further comprises a power supply.

8. The hardness tester in accordance with claim 6, wherein said counting circuit further comprises logic means for sensing the change of rotational direction of said encoding disk.

9. The hardness tester in accordance with claim 6, wherein said optical numerical display means comprising a plurality of alpha-numerical light emitting diodes.

10. The hardness tester in accordance with claim 6 further comprising:
  means for selecting a hardness scale from which the hardness number of said specimen is to be determined; and
  means for setting the count of said counting circuit to a predetermined number upon application of a reference load to said specimen, said predetermined number determined according to the hardness scale selected, and said predetermined number adjusting the count of said counting circuit so that the hardness number of the specimen as determined by the count of said count circuit is in accordance with the selected hardness scale.

11. The hardness tester in accordance with claim 2, wherein said encoding disk comprising 640 slots formed therein.

12. In the method for determining the hardness number of a specimen which utilizes a hardness tester having a penetrator with means for applying a load to said penetrator for forming an indentation in the specimen, the linear dimension of the resulting depth of indentation being determinative of the hardness value of a tested specimen, said loading means being rotationally actuated longitudinally, the rotational displacement of said loading means having a predetermined relationship to the linear dimension of the resulting depth of penetration, wherein the improvement comprises the steps of:

encoding the rotational displacement of said loading means into an electrical count by emitting a light signal parallel to said loading means, rotating an encoding disk containing a plurality of radially extending slots in alignment with said light signal and in close proximity to the periphery of said disk unitarily with said loading means receiving said light signal as transmitted through said encoding disk and converting said light signal into an electrical count;

decoding said count into a numerical value indicative of the depth of penetration into a tested specimen;

converting said value of depth of penetration to a hardness number;

displaying said hardness number on a visually discernible numerical display means.

13. In combination with a hardness tester including:
a. support means;
b. anvil means adjustably mounted in said support means for supporting a specimen to be tested;
c. a specimen penetrator mounted in said support means for movement along a penetration axis;
d. a spindle assembly threadedly engaged in said support means for movement along said axis to apply a load to said penetrator;
e. rotatable means for actuating said spindle assembly;
f. means including a load spring imposed between said spindle assembly and said penetrator for measuring the load applied to said penetrator; and
g. means drivingly engaged with said spindle assembly for measuring the movement of said penetrator along said axis; improved means for measuring the amount of said penetration along said axis comprising:
h. an electro-optical mechanical encoding means for producing an output electrical signal which comprises:
  (1) a pair of light radiation emitting devices;
  (2) a pair of light radiation sensing devices in optical alignment with said light emitting devices, said sensing devices adapted for emitting an output electrical signal indicative of the light sensed;
  (3) a mask member, fixedly disposed between said light emitting and sensing devices, said mask member having formed therein a radical segment of slots in optical alignment with said light radiation emitting and sensing devices; and
  (4) an annularly shaped encoding disk having a plurality of slots formed along its periphery, said encoding disk mounted on said loading means and rotatable therewith, said encoding disk slots disposed between and in optical alignment with said mask member slots and said light radiation sensing means, spacing between said mask member slots differing from the spacing between said disk slots such that upon the emission of light from said emitting devices and through said mask and disk slots a light interference pattern falls on said light radiation sensing devices, said interference pattern changeable with each rotation of said disk an angular distance substantially equal to one disk slot, said changeable light radiation interference pattern adapted to cause said light radiation sensing means to emit electrical signals in the form of digital binary information signals upon rotation of said disk an angular displacement substantially equal to one disk slot;

i. receiving means for said output electrical signal for converting said output electrical signal to an intermediate electrical signal corresponding to hardness number of said specimen; and
j. optical display means receiving said intermediate signal, for visually displaying said hardness number.

14. A hardness tester comprising:
a. a frame including means for holding a hardness test specimen;
b. a penetrator, slidably mounted on said frame for linear movement along an axis, for indenting said specimen;
c. rotatable means for actuating said loading means comprised of a hand wheel, rotational displacement of said loading means correlating with linear displacement of said penetrator;
d. a penetrator loading means further comprising:
  (1) a male loading spindle in threaded engagement with a female spindle, said male and female spindles carried by said frame, said male spindle rotatable in said female spindle by activation of said rotation means, the rotation of said male spindle causing linear loading displacement thereof;
  (2) a penetrator extension rod horizontally disposed in said frame along said penetration axis, said rod slidable in said frame and adapted for the mechanical attachment of said penetrator to an end thereof;
  (3) a load spring assembly disposed between said penetrator extension rod and said male load spindle, the loading of said male spindle being transferred by said spring assembly to said penetrator for loading displacement thereof and said load spring assembly adapted for measuring the load applied to said penetrator;
e. electro-optical mechanical encoding means further comprising:
  (1) a pair of light radiation emitting devices;
  (2) a pair of light radiation sensing devices in optical alignment with said light emitting devices, said sensing devices adapted for emitting an output electrical signal indicative of the light sensed;
  (3) a mask member, fixedly disposed between said light emitting and sensing devices, said mask member having formed therein a radial segment of slots in optical alignment with said light radiation emitting and sensing devices; and
  (4) an annularly shaped encoding disk having a plurality of slots formed along its periphery, said encoding disk mounted on said loading means and rotatable therewith, said encoding disk slots disposed between and in optical alignment with said mask member slots and said light radiation sensing means, spacing between said mask member slots differing from the spacing between said disk slots such that upon the emission of light from said emitting devices and through said mask and disk slots a light interference pattern falls on said light radiation sensing devices, said interference pattern changeable with each rotation of said disk an angular distance substantially equal to one disk slot, said changeable light radiation interference pattern adapted to cause said light radiation sensing means to emit electrical signals in the form of digital binary information signals upon rotation of said disk an angular displacement substantially equal to one disk slot;

f. receiving means for said output electrical signal for converting said output electrical signal to an intermediate electrical signal corresponding to hardness number of said specimen; and g. optical display means receiving said intermediate signal, for visually displaying said hardness number.

15. The hardness tester in accordance with claim 14, wherein said male spindle is about one-half inch in its outside diameter and threaded to 40 threads per inch.

16. Portable apparatus for testing hardness of specimen materials, specimen hardness being determined by depth of penetration of the specimen by a penetrator when a predetermined load is applied thereto, depth of penetration for said predetermined load defining an arbitrary hardness number, comprising:

a. frame including means for fixedly supporting a test specimen;

b. said penetrator being mounted in an assembly on said frame and movable linearly longitudinally therealong to contact said specimen;

c. loading means for applying a predetermined load to said penetrator upon contact thereof with said specimen;

d. rotatable means for linearly moving said loading means and thereby moving said penetrator into contact with said specimen, angular displacement of said rotatable means correlating unitarily with linear displacement of said penetrator when loaded by said loading means;

e. electromechanical optical encoding means connected to said rotatable means, for producing electrical coded signals proportional to angular displacement of said rotatable means from a reference position defined by said penetrator contacting said specimen before said predetermined load is applied;

f. optical display means for sensing said electrical signals, converting the signals to an intermediate electrical signal and displaying a digital representation proportional thereto, said digital representation corresponding to said arbitrary hardness number of said specimen.

* * * * *